(12) United States Patent
Bailey et al.

(10) Patent No.: US 9,060,717 B2
(45) Date of Patent: Jun. 23, 2015

(54) DETECTION AND MEASUREMENT OF TISSUE IMAGES

(71) Applicant: The Ohio State University, Columbus, OH (US)

(72) Inventors: Melissa D. Bailey, Gahanna, OH (US); Chiu-Yen Kao, Claremont, CA (US)

(73) Assignee: THE OHIO STATE UNIVERSITY, Columbus, OH (US)

( * ) Notice: Subject to any disclaimer, the term of this patent is extended or adjusted under 35 U.S.C. 154(b) by 317 days.

(21) Appl. No.: 13/757,243

(22) Filed: Feb. 1, 2013

(65) Prior Publication Data

US 2013/0201450 A1 Aug. 8, 2013

Related U.S. Application Data

(60) Provisional application No. 61/594,027, filed on Feb. 2, 2012.

(51) Int. Cl.
*A61B 3/14* (2006.01)
*A61B 3/10* (2006.01)
*G06T 7/00* (2006.01)
*A61B 19/00* (2006.01)

(52) U.S. Cl.
CPC . *A61B 3/14* (2013.01); *A61B 3/102* (2013.01); *A61B 19/5225* (2013.01); *A61B 19/5244* (2013.01); *G06T 2207/30041* (2013.01); *G06T 7/0081* (2013.01); *G06T 2207/20161* (2013.01)

(58) Field of Classification Search
CPC ...... A61B 3/1025; A61B 3/14; A61B 5/0066; A61B 19/5225; A61B 19/5244
USPC ............... 351/205, 206, 246; 606/5
See application file for complete search history.

(56) References Cited

U.S. PATENT DOCUMENTS

2014/0029820 A1* 1/2014 Srivastava et al. ............ 382/131

OTHER PUBLICATIONS

Kao, Chiu-Yen, et al., "Semiautomatic Extraction Algorithm for Images of the Ciliary Muscle," Optometry and Vision Science, vol. 88, No. 2, 2011, pp. 275-289.

* cited by examiner

*Primary Examiner* — Huy K Mai
(74) *Attorney, Agent, or Firm* — Meunier Carlin & Curfman LLC

(57) ABSTRACT

A system and method of measuring a tissue structure is provided. The method includes obtaining image data of the tissue structure. Also, an anatomical landmark in the image data is identified. A first geometric shape is applied to the image data of the tissue structure based on the anatomical landmark. For example, the geometric shape may have a linear portion, such as a square or diamond. The method also includes applying a second geometric shape to the image data of the tissue structure based on the anatomical landmark. The second geometric shape may be different than the first geometric shape, such as an arc or parabola. The method also includes segmenting a first substructure of the image data from a second substructure of the image data. These substructures may be, for example, a sclera and ciliary body of an eye.

29 Claims, 11 Drawing Sheets

DETECTION AND MEASUREMENT OF TISSUE IMAGES

RELATED APPLICATIONS

This application claims the benefit of U.S. Provisional Application No. 61/594,027 filed on Feb. 2, 2012 entitled "Semiautomatic Extraction of Algorithm for Images of the Ciliary Muscle" and which is hereby incorporated in its entirety by reference.

ACKNOWLEDGMENT OF GOVERNMENT SUPPORT

This invention was made with government support under grants nos. NCRR(NIH)KL2RR025754 and NEI(NIH) R24EY014792 awarded by the National Institutes of Health. The government has certain rights in this invention.

BACKGROUND

The traditional method for imaging the ciliary body in clinical practice and research is ultrasound biomicroscopy (UBM). Recently, the development of the Zeiss Visante™ Anterior Segment Optical Coherence Tomographer (OCT, Carl Zeiss Meditec) has allowed for non-contact imaging of the ciliary body. OCT measurements, for example, have enabled pediatric studies of the relationship between refractive error and ciliary body dimensions and between accommodative microfluctuations and ciliary body dimensions.

SUMMARY

A method of measuring a tissue structure is provided. The method includes obtaining image data of the tissue structure. Also, an anatomical landmark in the image data is identified. A first geometric shape is applied to the image data of the tissue structure based on the anatomical landmark. For example, the geometric shape may have a linear portion, such as a square or diamond. The method also includes applying a second geometric shape to the image data of the tissue structure based on the anatomical landmark. The second geometric shape may be different than the first geometric shape, such as an arc or parabola. The method also includes segmenting a first substructure of the image data from a second substructure of the image data.

These substructures may be, for example, a sclera and ciliary body of an eye. (Ciliary body as used herein may include only the muscle structures or other, additional structures of the ciliary anatomy within the eye.) The anatomical landmark may be a scleral spur. The image may be measured and compared to epidemiological data to develop systems for addressing maladies such as using the eyes to focus during reading or myopia development in children or for presbyopia in adults. It could be used to study the eye and experimental conditions in non-human species as well.

The method may also include obtaining background image data with the image data of the tissue structure. The background image data is separated from the tissue structure image data. The method may also include downsizing or compressing the image data.

Each geometric shape may define a segmentation region. The second geometric shape may be an approximation of an ocular structure. The first geometric shape may be a diamond shape adapted to the shape of a portion of the ciliary body. The diamond shape may be positioned on the apex of the ciliary body.

The method may also include dilating a threshold region with a rolling ball. Applying the first geometric shape and dilating the threshold region may include forming an outline of at least a portion of the ciliary body.

Applying the second geometric shape may also include fitting a curve through the anatomical landmark. For example, the method may include fitting a parabola through the scleral spur. The method may also include using the outline to locate a second point and third point. Fitting the curve may also include fitting the parabola through the scleral spur and the third point.

In addition, the method may include locating a fourth point positioned above a straight line extending through the scleral spur and the third point. And, the method may fit the parabola through the scleral spur, the third point and the fourth point. The parabola, for example, may define an upper boundary between the ciliary boundary and the sclera.

The parabola may be adjusted by minimizing the energy of the image data. The parabola may also be adjusted using a least squares fit.

The method may also include applying different indexes of refraction to the sclera and the ciliary body.

The method may also include removing the iris from the image using the second point and the scleral spur.

Also, the method may include measuring one or more characteristics of the ciliary body, such as the thickness, area, volume, etc.

DETAILED DESCRIPTION

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

I. Inventors' Identification of the Problem

The inventors have identified several shortcomings in the prior art technology. OCT instruments are becoming valuable tools for imaging human tissue. But, a raw image obtained from these instruments may be subject to distortions due to non-linear axial scanning, non-telecentric scanning, and lack of correction for the refractive properties of the tissue that is imaged. While the prior art suggests the manufacturer has addressed these distortions when the Visante™ is used to image and measure the anterior segment, the Visante™ was not designed to image and measure the ciliary body.

In measuring the ciliary body with the calipers in the Visante™ software in previous studies, the inventors discovered several inadequacies of the calipers when used in ciliary body images that prompted them to begin analyzing a raw format of the images, i.e., binary files, in third-party software. Using a raw format of the images has also inspired their evaluating distortions in the images.

The first inadequacy they noted was that it is impossible for the investigator who acquired the images to make measurements in a masked fashion.

Figure 1:
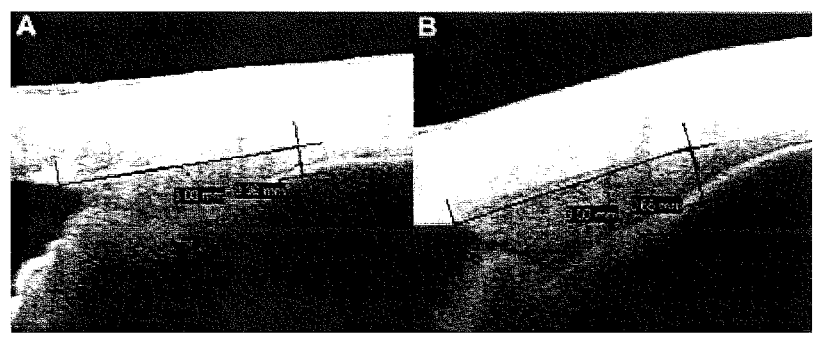
FIG. 1A is an image of a scleral spur with caliper determination of a desired measurement distance from the scleral spur.
FIG. 1B is an image of another scleral spur with caliper determination of a desired measurement distance from the scleral spur.

Second, the calipers in the Visante™ software are straight lines, and in some patients, the sclera is curved. When calipers are used to locate the desired measurement distance from the scleral spur, they cut across ciliary body rather than follow the curvature of the sclera, as shown in FIG. 1. In their previous studies using the calipers in the Visante™ software, the inventors noted that some subjects had a flatter scleral curvature, while other subjects had a steeper scleral curvature. These scleral curvature differences could lead to an increased variability in the ciliary body thickness measurements, especially as measurements are made at an increasing distance from the scleral spur.

Third, the Visante™ software is not programmed to apply an appropriate refractive index or scaling factor to the image of the sclera and ciliary body. It is therefore not able to make measurements of ciliary body thickness that are in the range of a physiologically accurate measurement.

Finally, measurements of the cross-sectional area cannot be made using tools available within the Visante™ software. But, these measurements may be critical to understanding changes in the ciliary body with presbyopia or other maladies.

To address these inadequacies, the inventors developed a semi-automatic (or potentially fully automatic) extraction algorithm or process to objectively and accurately measure the dimensions of the ciliary body. The algorithm uses active contour models that can produce sub-pixel accuracy of object boundaries, incorporate regional information for robust segmentation, and provide smooth and closed contours of the object of interest. In particular, the inventors employ an active contour model based on a local binary fitting energy to segment magnetic resonance images with intensity inhomogeneity. The inventors extended the model to outline the boundary of the ciliary muscle.

In order to avoid image alteration created by the Visante™ software when generating a jpeg file, the inventors used the raw images in the form of binary files that were exported from the Visante™. They also assessed the raw images for distortions.

The inventors demonstrated that the binary files exported from the Visante™ provide renderings of the structure of human sclera and ciliary muscle are free from geometric distortions and that the semi-automatic algorithm is capable of segmenting the ciliary muscle in Visante™ images and providing a repeatable measurement.

II. Some General Implementations of the Invention

One implementation of the present invention includes a method of measuring a tissue structure having multiple expected shapes. The method includes obtaining image data of the tissue structure. An anatomical landmark is then identified in the image data of the tissue structure. The method includes applying a first geometric shape to the image data of the tissue structure based on the anatomical landmark. The first geometric shape may include at least one linear portion. Also, the method may include applying a second geometric shape to the image data of the tissue structure based on the anatomical landmark. The second shape may, for example, including at least one curved portion. The method may also include segmenting a first substructure of the image data from a second substructure of the image data using the first and second geometric shapes.

III. Implementation for Measuring Ciliary Body

Figure 2:
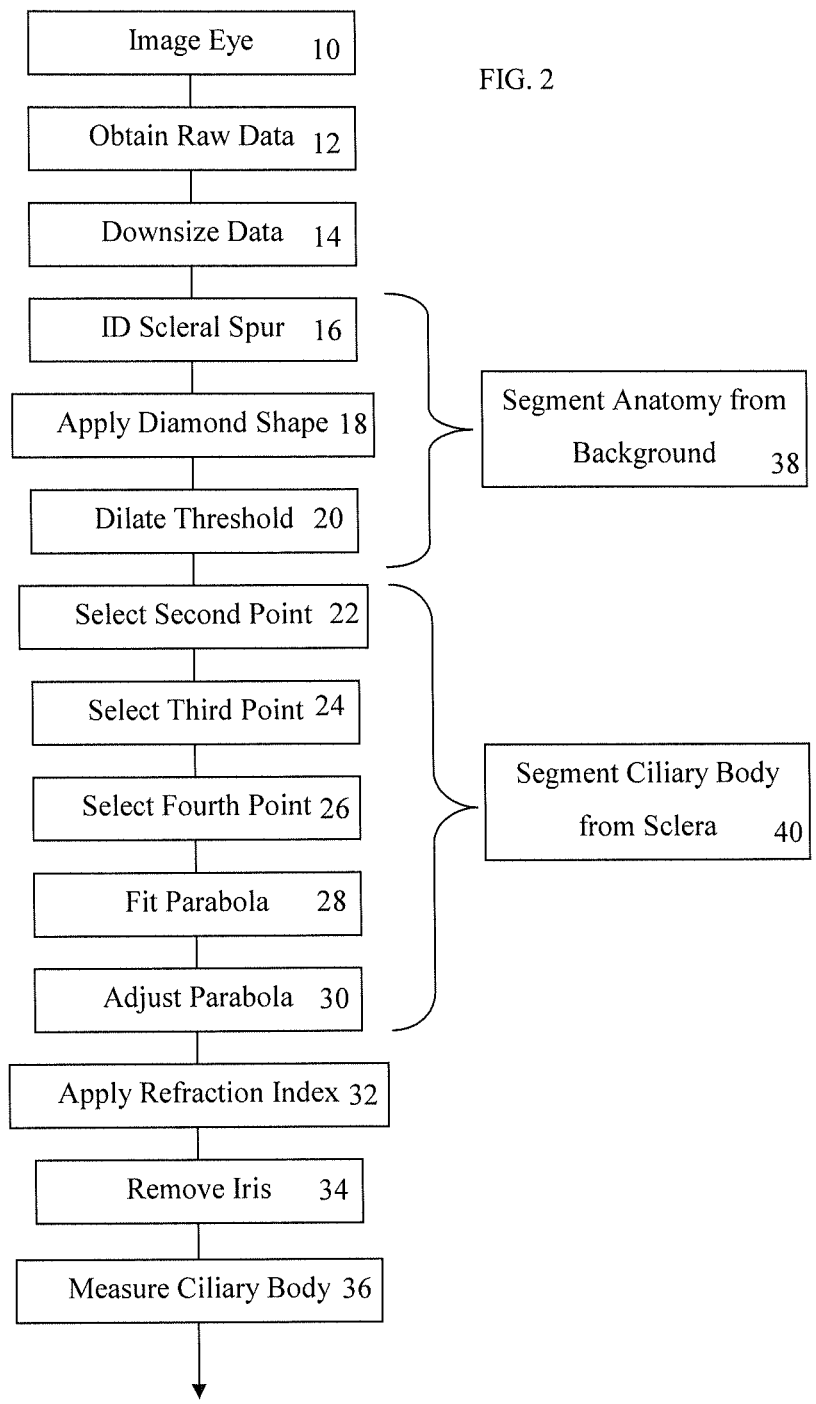
FIG. 2 is a schematic or flow diagram of a method or process for measuring a ciliary body.

As shown in FIG. 2, the method or process may be adapted to specifically measure a ciliary body of the eye. Generally, the method includes two broader steps of 1) segmenting 38 the anatomical structures, including the ciliary body and the sclera from the background and 2) segmenting 40 the ciliary body from the sclera. The ciliary body, once well-segmented, can be analyzed for various one, two and three dimensional (and possible over time) characteristics.

The term "ciliary body" herein may include the ciliary muscle and the ciliary processes. In OCT measurements the ciliary processes are generally not visible, but could show up in other types of scans or imaging. Regardless, the term "ciliary body" is defined as those structures that are actually distinguishable using the scanning technique used to collect the data. The "ciliary body" therefore may only be the ciliary muscle in OCT scans.

The method includes imaging the eye 10, such as via an OCT scan. Raw data is obtained 12 from the eye imaging either because it was obtained from a third party or actually generated as the initial step in the process. This data may be downsized 14 or compressed to reduce the computational expense of executing the process.

Using the image data, the sclera spur is identified 16 either visually by an operator or automatically or some mixture of the two. (Notably, all steps herein may be manual, semi-automatic or fully automatic.) A diamond shape is applied 18 with reference to the scleral spur to define a first segmentation region separating the ocular anatomy from the background. A threshold between the background and the sclera and the background is dilated 20, such as by using a rolling ball.

Then, (as described more below) additional reference points are selected to help segment the ciliary body from the sclera, such as a second 22, third 24 and fourth 26 points. A parabola is fit 28 through the scleral spur, the third and fourth points. The method then may include adjusting the parabola 30 through some iterative algorithm, such as an energy minimization or least-squares fit.

The method may also include applying a refraction index 32 to the sclera and the ciliary muscle. The iris may also be removed 34 to further improve the segmentation of the ciliary body. The ciliary body may then be measured 36 a number of ways, including thickness, area and volume calculations. Volume calculations may be yielded, for example, if several segmented ciliary body images are stacked with 3-D scanning. Also, changes of the ciliary body over time may be quantified.

A. Determination of Refraction Index

The inventors determined with foundational research whether the raw scanning data would benefit from application of a refraction index.

Figure 3:
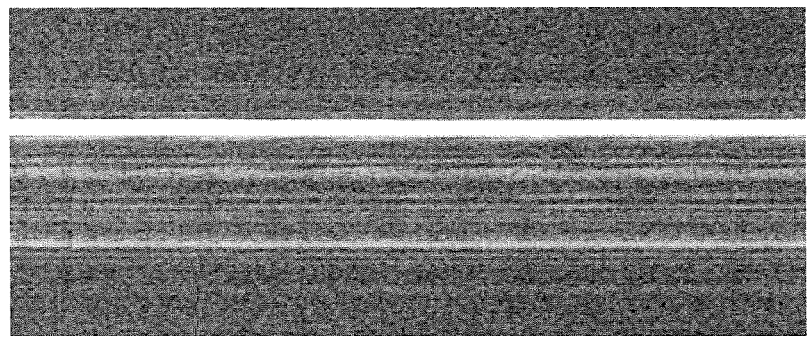
FIG. 3 is a Visante™ image of the front surface of an optical flat (bright white line)

To evaluate the extent of geometric distortion in images, an optical flat (Edmund Optics, fused silica, n=1.458, certified flat to within ¼ wavelength) was imaged with the Visante™ in a manner identical to imaging procedures described below for ciliary body imaging. FIG. 3 is an image of the optical flat in Enhanced High Resolution Corneal Mode. Note that the image appears to be flat, with no distortion of curvature in the periphery of the image. When the binary file for this image was imported into Matlab®, the y-coordinates of the center of the reflection of the surface of the optical flat varied by only 1 to 2 pixels across the length of the image.

An additional experiment was conducted to evaluate the multiple distortions (geometric and refractive) of images of the sclera and ciliary body. Human eye tissue (right eye, 37-year-old, white male, fixed in 10% formalin) was obtained from the National Disease Research Interchange (NDRI). A small section of sclera and ciliary muscle tissue (FIG. 4A) was imaged using both the Visante™ and digital photography. The anterior-posterior length of the tissue was selected such that the anterior and posterior cut ends of the tissue were visible within the lateral imaging view of the Visante™ in enhanced high-resolution corneal mode. Once the tissue had been sectioned from the globe, the iris tissue in the section stuck to the inner wall of the limbus/cornea rather than remaining suspended in what used to be the anterior chamber, so the iris was removed to make imaging and tracing (described below) easier. Then, the tissue was positioned on a piece of foam board such that the scleral wall was perpendicular to the surface of the board. The tissue was held in the perpendicular position with very thin sewing needles (Richard Hemming & Son, Large Eye Needles, Betweens Size 12, England). The sewing needles were positioned in the anterior chamber angle and at the posterior end of the scleral wall and ciliary body (FIG. 4A) so that they would not block the scanning beam of the Visante™ in the thicker, more anterior portion of the ciliary body.

In imaging the tissue with the Visante™, the wall of the sclera was positioned orthogonal to the instrument's scanning beam. Otherwise, the path length of the infrared light through the tissue would be artificially increased due to the tissue tilt, and subsequent registration of the Visante™ images with photographs of the tissue would have reduced accuracy. To appropriately position the tissue, the operator of the Visante™ was careful to have the foam board parallel to the floor. The inventors determined that if the eye of one sewing needle were placed flat against the scleral wall, the Visante™ would image through the eye of the needle when the tissue was aligned orthogonally to the scanning beam in that dimension. The shadow cast by the needle along the scleral wall is visible in FIG. 4B. Thus, tilt or turn about the horizontal axis was monitored by ensuring the foam board was parallel to the floor and about the vertical axis by insuring the Visante™ was imaging through the eye of the needle. The scanning beam in the Visante™ appears as a visible horizontal line of light on the eye (or tissue) during imaging, and this horizontal line was always at the cut edge of the tissue that was furthest from the foam board. This meant the Visante™ was imaging the same portion of tissue that was photographed.

Figure 4:
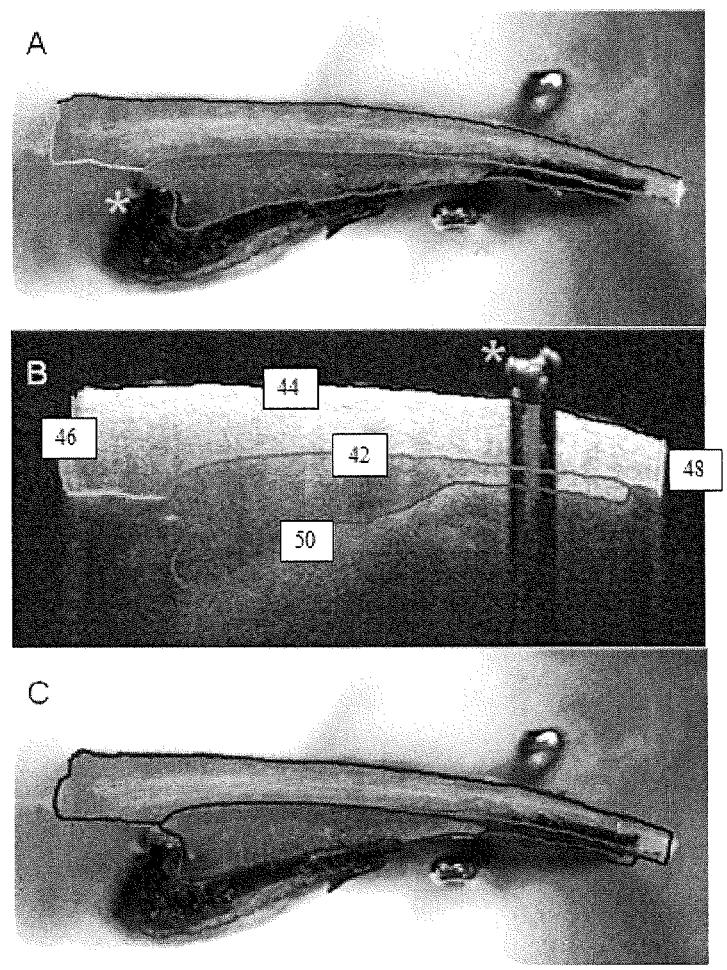
FIG. 4A is a photograph of a human donor sclera and body tissue with outlined anatomical structures.
FIG. 4B is a Visante™ image of the sclera of FIG. 4A with outlined anatomical structures.
FIG. 4C is a registration of the outlined anatomical structures of FIG. 4B onto the photograph of FIG. 4A.

The same piece of tissue was also digitally photographed. The tissue was placed in front of the camera so that the cut edge, a cross-sectional view of the sclera and ciliary body, was visible. Photographs were taken only when the tissue was positioned so that the camera operator could not see down the wall of the sclera or the down the inner surface of the ciliary body, i.e., only the cross-section of tissue was visible. The only exception to this was at the most posterior end of the sclera/ciliary body. This portion of the tissue was the thinnest and it was difficult to get the wall of the sclera perpendicular to the foam board at this location; it tended to bend slightly (FIG. 4A). Inventors accounted for this problem when completing the registration of the Visante™ images with the photographs by biasing the registration calculations to align the more anterior portions of the sclera/ciliary body where the tissue did not bend.

To facilitate registration of the photographs and the Visante™ images of the tissue, both were outlined in Photoshop (Adobe, San Jose, Calif.). In the Visante™ images (FIG. 4B), the inner line 42 and outer line 44 and the cut ends 46, 48 of the sclera were traced, and the ciliary body was also traced along the heavier white boundary in the image that was created by the ciliary pigmented epithelium (line 50). In the photographs (FIG. 4A), the sclera was traced in an identical manner as in the Visante™ images, and the ciliary body was also traced along the ciliary pigmented epithelium because it was assumed that the highly pigmented processes and folds of the pars plicata would not be visible in Visante™ images.

The Visante™ images were then registered to photographs using rigid transformation which includes translation, rotation, and uniform scaling. The inventors first registered the outer surface of the sclera and the cut ends of the sclera 44, 46 and 48 because the infrared scanning beam in these portions of the image would be traveling in air. Before entering the tissue, the index of refraction was set at n=1.0. Registration of the entire image to align these edges accounted for simple magnification differences between the Visante™ images and the photograph, i.e., the differences that were not due to the path length of the infrared light through the sclera and ciliary body.

After these lines were registered, one single adjustment in the y-dimension of the image. This alignment provided very close alignment of the lines 42 and 50 (FIG. 4C) without any additional adjustments. In other words, the entire width of the image was registered with only a refractive adjustment and no geometric adjustments for distortion were needed. This procedure was repeated with 16 different pairs of photographs and Visante™ images of the tissue. The mean±SD adjustment along the axial scan depth that was required to register the scleral and ciliary body in the image pairs was 1.5586±0.05, i.e., the index of refraction for the infrared light traveling through the sclera and ciliary body fixed in 10% formalin was established at n=1.56. FIG. 4C shows the outline of the sclera and ciliary body from a Visante™ image (blue lines) after it has an appropriate refractive index applied to the scleral and ciliary body areas of the image (n=1.56). Note that a single refractive index can be applied to create an acceptable image registration for both the inner scleral wall and the ciliary pigmented epithelium (FIG. 4C).

Previously publications have reported the index of refraction or scaling factor for rabbit sclera and ciliary body to be 1.41 and 1.38, respectively. Bovine muscle tissue and human cardiac muscle were also reported to have a refractive index of 1.38. The slightly higher value reported here (n=1.56) may be due to fixation of the tissue or slight tilting of the tissue during imaging with the Visante™. Nonetheless, the imaging of the optical flat and the tissue registration process demonstrated that the binary files from the Visante™ provide images without geometric distortions, and that the refractive indices of human sclera and ciliary muscle are probably very close to each other and close to what has been reported for the rabbit. The inventors believe a range of these values from 1.38 to 1.56 may be used in the measurement process, including different indices for different types of tissue.

B. Semi-Automatic Extraction Algorithm

1) Preparing the Images for Analysis: Region of Interest and Down-Sampling

Figure 6:
FIG. 6 is an example of an image of the ciliary body that was exported from the Visante™ as a binary file.

For the semi-automatic algorithm, raw images (refractive index of 1.0) of the ciliary body and sclera were exported as binary files (.bin) using the Visante™ OCT Image Exporter software. The images were then imported into Matlab for extraction with the semi-automatic algorithm as described in detail below. The raw images acquired with the Visante™ were grey-scale images of size 512 by 1024 pixels (4 cm by 10 cm) (FIG. 6). The images were resized to 512 by 1280 pixels (1:2.5, and 128 pixels per mm) so that the images could be visualized in the original aspect ratio. In Matlab, resizing is implemented as B=imresize(A, [512, 1280], 'bicubic') which resizes image A to image B (512 by 1280 pixels) by applying a low-pass filter before the bi-cubic interpolation to reduce aliasing.

An initial step was to manually select the location of the scleral spur. One experienced investigator and one trained investigator visually inspected the image and clicked on the scleral spur (FIG. 6, asterisk). The mean (±SD) distance of the location of three selections of the scleral spur was 3.98 (±2.89) pixels from the mean location of the scleral spur. Because of this minor variation in the selection of the scleral spur, the scleral spur was manually selected three times for each image. The mean coordinates of the three selections was used as the final location of the scleral spur in subsequent processing. This process was then repeated by both investigators a second time so that the within-investigator variance could be determined.

The horizontal dimension of the image was cropped to include the area of primary interest, i.e., the ciliary body, at 128 pixels to the left and 768 pixels to the right of the scleral spur. The cropped image dimensions were 512 by 896 pixels (FIG. 6). Because Visante™ images are high-resolution, processing the original raw images is time intensive. The time required for analysis was reduced by down sampling the images to one-fourth their original size prior to analysis. In Matlab, this was implemented by using B=imresize (A,¼, 'bicubic').

2) Region-Scalable Image Segmentation Algorithm

Step 1: Extracting the Ocular Structure from the Background

The first step in the region-scalable image segmentation algorithm was to delineate the ocular structures from the background. The otherwise dark ciliary body area was thus extracted from the other, lighter, ocular structures such as the sclera. The process of delineation is illustrated by the white outlines in FIGS. 7A-D. A region-based segmentation model, that used the intensity information in local regions at a controllable scale, was employed. The function used in Step 1 is provided below in the section entitled "Region Scalable Fitting Energy Algorithm."

Figure 7A:
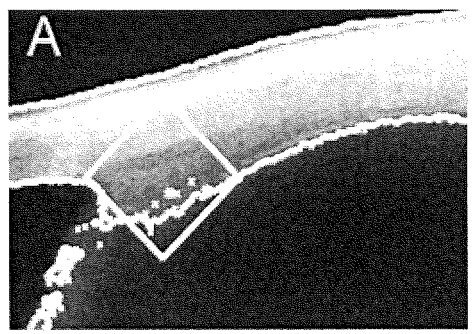
FIGS. 7A-7D illustrate segmentation of the ciliary body and sclera from background information.
Figure 7B:
Figure 7C:
Figure 7D:

The delineation process began by generating an approximation of the shape of the ocular structures (curve=Γ) to serve as a starting point (which was represented as [X|ϕ(X)=0]). The initial approximation was generated by finding the region where the pixel intensity was greater than the mean. However, the boundary of this region was not always smooth and could contain multiple sub-regions of pixel intensity (FIG. 7A). Furthermore, the region near the apex of the ciliary body was darker and usually was not identified by this thresholding technique. Thus, the inventors included a diamond shape with 256 pixels in diagonal direction. The diamond shape can range from 0.6 mm to 1 mm edge length depending upon the size of the tissue being measured. Dilating the union of diamond shape region and the thresholding region with a rolling ball with a 5 pixel radius gave a better initial approximation of the outline (FIG. 7B). From this initial outline, the outline of the ocular structures evolved according to the model described below and approached the boundary of the sclera and ciliary body as shown in FIGS. 7C and 7D. The final outline is depicted in FIG. 7D.

Figure 8A:
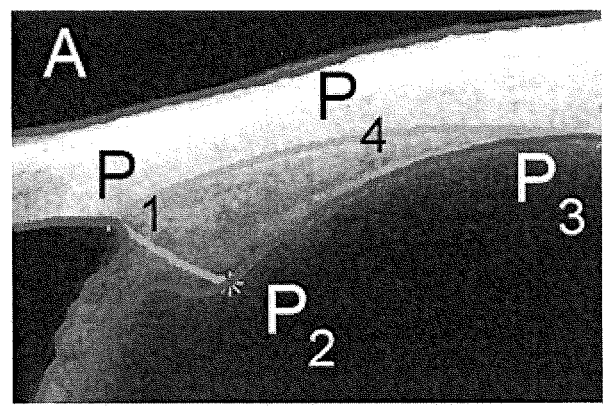
FIGS. 8A-8C illustrate segmentation of the ciliary body from the sclera.

Step 2: Extracting the Ciliary Body from the Ocular Structures:

An approximation of the initial contour of the ciliary body (FIG. 8) was based on the histological data from the literature, indicating that the ciliary body was usually 4-6 mm long and 1-2 mm wide at the point of greatest thickness. In FIG. 8A, p1 is the location of the manually-selected scleral spur (described above). The second and third points (p2 and p3) were automatically selected by the algorithm on the lower branch of the lower curve, 1.2 mm and 6 mm from the sclera spur in the horizontal direction, respectively. A point 0.5 mm above a line from p1 to p3 and half way between p1 and p3 served as the fourth point (p4). A parabola was constructed passing though p1, p4, and p3. This generated a reasonable guess of the upper boundary of the ciliary body. Connecting all the points created an initial closed contour approximation for the outline of the ciliary body (FIG. 8A).

Figure 8B:
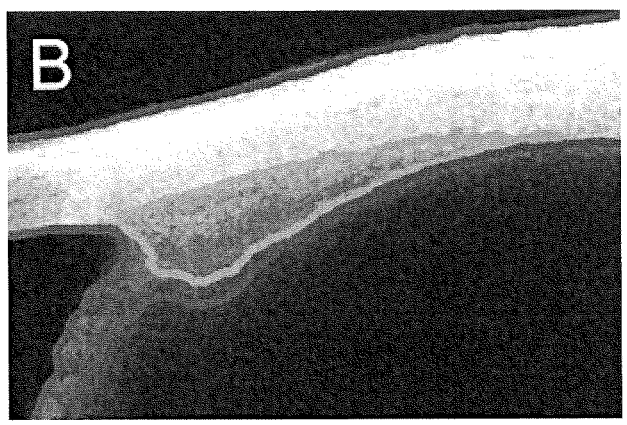

Instead of considering the whole image domain, (FIG. 6), only the energy defined on the region inside of the red curve (FIGS. 8A-C) was considered (as described in more detail below). When the energy was minimized, the curve stopped at the boundary of ciliary body/sclera. The contour of the ciliary body was then fine-tuned by repeating the algorithm on the high-resolution images, i.e., the original image prior to down-sampling, for a few time steps until it converged (FIG. 8B).

Figure 8C:

An index of refraction of 1.41 was applied to the region of the sclera and an index of refraction of 1.38 to the region of the ciliary body to shrink that portion of the image in the y-dimension only so that it represented an appropriate axial scan depth for subsequent measurements. A least squares method was used to fit a parabola to the upper contour of the p1-p4-p3 curve. The region of ciliary body was segmented by selecting the region below the parabola (p1-p4-p3) that was inside the outline of the sclera and ciliary body (p2-p3). When a segment of the iris was visible in the images, it was removed by following the curve below scleral spur from p1 to p2. The final result of the algorithm is shown in FIG. 8C. Note that the sclera and ciliary body sections of the image in FIG. 8C have been adjusted to a refractive index of n=1.41 and 1.38, respectively, and that this region is noticeably thinner than before this refractive index is applied (FIG. 8C).

C. Ciliary Body Measurements

Figure 9:
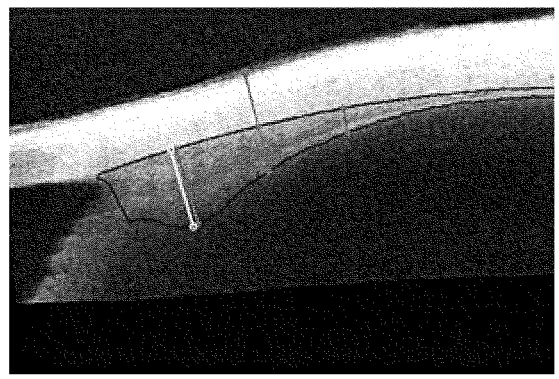
FIG. 9 illustrates measurements being made of the ciliary body from FIGS. 8A-8C.

Based on the final ciliary body outline in FIG. 8C, thickness measurements were then obtained at 1 mm, 2 mm, and 3 mm (CBT1, CBT2, CBT3) posterior to the scleral spur (FIG. 9). In addition, the thickest measurement of the ciliary body (CBTmax) was identified. The cross-sectional areas of portions of the first three millimeters of the ciliary body (CBA1, CBA2, and CBA3) were also measured. Measurements were made by counting the pixels in each portion and multiplying by the image resolution (1 mm=128 pixels). These measurement points were chosen for this initial investigation, but once the ciliary body is outlined, it is possible to obtain ciliary body or scleral measurements at any location with this algorithm.

D. Region Scalable Fitting Energy Algorithm

The region-scalable fitting energy was defined in terms of a contour Γ and two fitting functions and that locally approximate the image intensities outside and inside of the contour. This energy was incorporated into a variational level set formulation with a level set regularization term. The energy was defined as follows:

$$F(f_1, f_2, \Gamma) = \lambda_1 \int_\Omega \left[ \int_\Omega K(x-y)|I(y) - f_1(x)|^2 H(\phi(y)) \, dy \right] dx +$$
$$\lambda_2 \int_\Omega \left[ \int_\Omega K(x-y)|I(y) - f_2(x)|^2 (1 - H(\phi(y))) \, dy \right] dx +$$
$$v \int_\Omega \frac{1}{2} (|\nabla \phi(x)| - 1)^2 dx + \mu \int_\Omega |\nabla H(\phi(x))| dx$$

where , , , and were nonnegative constants, Ω was the domain of down-sampled image, ϕ was a level set function whose zero level set was the contour, H was the Heaviside function, and K was the kernel function. The kernel function K was chosen as a Gaussian function:

$$K(x) = \frac{1}{(2\pi)^{n/2} \sigma} e^{-|x|^2/2\sigma^2}$$

where σ was a scale parameter that controls the scale of the effective neighborhood. The first two terms in $F(f_1, f_2, \Gamma)$ were the local binary fitting energies. The third term was the level set regularization term used to penalize the deviation of the level set function from a signed distance function, and the last term was the length term to regularize the contour. Minimizing the energy function $F(f_1, f_2, \Gamma)$ provided a smooth contour Γ which separated the foreground (inside of Γ) and background (outside of Γ) regions and a good intensity fitting pair ($f_1$, $f_2$) inside and outside of the contour. The standard gradient descent method was used to minimize the energy function $F(f_1, f_2, \Gamma)$. By calculus of variations, it can be shown that the functions ($f_1$, $f_2$) that minimize $F(f_1, f_2, \Gamma)$ satisfy $$f_1(x) = \frac{K_\sigma(x) * [H(\phi(x))I(x)]}{K_\sigma(x) * H(\phi(x))}$$

$$f_2(x) = \frac{K_\sigma(x) * [(1 - H(\phi(x)))I(x)]}{K_\sigma(x) * [1 - H(\phi(x))]}$$

and φ satisfies $$\frac{\partial \phi}{\partial t} = \delta(\phi) \begin{bmatrix} -\lambda_1 \int_\Omega K_\sigma(y-x)|I(x) - f_1(y)|^2 \, dy + \\ \lambda_2 \int_\Omega K_\sigma(y-x)|I(x) - f_2(y)|^2 \, dy + \\ \mu \nabla \cdot \left(\frac{\nabla \phi}{|\nabla \phi|}\right) + \nu \left(\Delta \phi - \nabla \cdot \left(\frac{\nabla \phi}{|\nabla \phi|}\right)\right) \end{bmatrix}$$

where δ is the Dirac delta function.

In the numerical implementation, the functions ($f_1$, $f_2$) were updated at every time step before the update of the level set function φ. The parameters are chosen as $\lambda_1 = \lambda_2 = 1$, $\nu = 1\mu = 0.1 \cdot 255^2$, and $\sigma = 3$.

In a second step of the image segmentation process, as described above, the energy is limited to the region inside the tissue boundary. For example, the functions below were applied within the boundaries defined in FIGS. 8A-8C.
The corresponding functions ($f_1$, $f_2$) that minimize $F(f_1, f_2, \Gamma)$ satisfy $$f_1(x) = \frac{K_\sigma(x) * [H(\phi(x))H(\phi_1(x))I(x)]}{K_\sigma(x) * H(\phi(x))H(\phi_1(x))}$$

$$f_2(x) = \frac{K_\sigma(x) * [1 - H(\phi(x))H(\phi_1(x))I(x)]}{K_\sigma(x) * [1 - H(\phi(x))H(\phi_1(x))]}$$

and φ satisfies $$\frac{\partial \phi}{\partial t} = \delta(\phi)H(\phi_1) \begin{bmatrix} -\lambda_1 \int_\Omega K_\sigma(y-x)|I(x) - f_1(y)|^2 \, dy + \\ \lambda_2 \int_\Omega K_\sigma(y-x)|I(x) - f_2(y)|^2 \, dy + \\ \mu \nabla \cdot \left(\frac{\nabla \phi}{|\nabla \phi|}\right) + \nu \left(\Delta \phi - \nabla \cdot \left(\frac{\nabla \phi}{|\nabla \phi|}\right)\right) \end{bmatrix}$$

The parameters are chosen as $\lambda_1 = \lambda_2 = 1$, $\nu = 1\mu = 0.01 \cdot 255^2$, and $\sigma = 3$.

IV. Experimental Data

For analyses described below that required comparison of the algorithm to caliper measurements from the Visante™ software, the inventors were unable to apply an appropriate refractive index to the area of the sclera and ciliary body because that is not an option available within the Visante™ software. So for the purposes of those algorithm-to-caliper comparisons, the inventors also obtained algorithm thickness measurements with a refractive index of 1.0 applied to the entire image.

A cross-sectional study of 26 subjects (21 female) between the ages of 19 and 40 years (mean±SD=25.3±5.0 years) was conducted. The mean±SD spherical equivalent refractive error was −3.39±3.4 D (range −11.03 D to +3.13 D). Subjects were required to have best-spectacle-corrected visual acuity better than 20/40 in each eye to assure proper target fixation during measurement, and all subjects were free of ocular disease other than refractive error. An effort was made to recruit subjects with a wide range of refractive error.

Refractive error and ciliary body thickness measurements were made under cycloplegic conditions on right eyes only. One drop of 0.5% proparacaine hydrochloride ophthalmic solution was given, followed by two drops of 1% tropicamide ophthalmic solution administered five minutes apart. Testing was completed 30 minutes after the first drop of tropicamide. Refractive error was measured with a Grand Seiko autorefractor. The mean spherical equivalent from five measurements was reported.

The nasal ciliary body of each subject was imaged through the sclera while the subject viewed an external target. Images were obtained in Enhanced High Resolution Corneal Mode, a high-resolution imaging mode available with the Visante™ 2.0 software. All images were obtained by the same investigator. Six images of the ciliary body were obtained, and the subject was re-aligned between each measurement.

Figure 5:
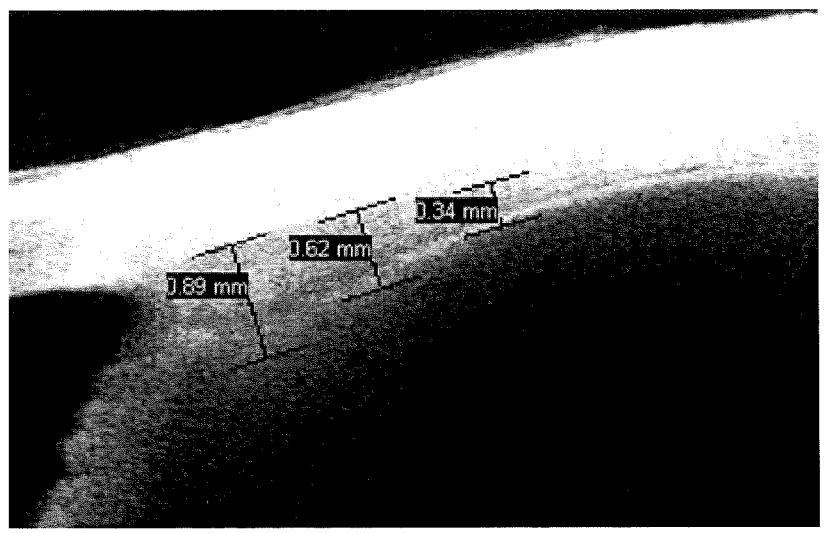
FIG. 5 is an image of a ciliary body showing three software caliper measurements, i.e., at 1 mm (CBT1), 2 mm (CBT2), and 3 mm (CBT3) posterior to the scleral spur.

When images were measured with the calipers, a uniform refractive index of 1.0 was applied to the entire image by editing the image so that both corneal surface lines were flat and at the very bottom of the image. Although there are estimates of the appropriate refractive index for the sclera/ciliary body in the published literature, it is not currently an option to incorporate this refractive index into measurements made with the calipers in the Visante™ software. Thickness measurements were obtained at 1 mm, 2 mm, and 3 mm posterior to the sclera spur (FIG. 5) using calipers in the Visante™ software. Thickness measurements were completed on each of the six images by one experienced investigator and one inexperienced investigator. Because the images and all other study measurements were acquired by a different investigator, both investigators making measurements with calipers were masked to the refractive error status of the study subjects. The data were entered into an Excel spreadsheet.

A. Statistical Analyses

1) Caliper and Algorithm Measurement Variability

As described above, thickness measurements, CBT1, CBT2, and CBT3 were made using both the algorithm and the Visante™ software calipers. Measurements of the thickest part of the ciliary body (CBTmax) and of the cross-sectional areas for the first 1 mm (CBA1), 2 mm (CBA2), and 3 mm (CBA3) of the ciliary body were only made with the algorithm. For each subject, measurements were made on each of six images.

Bland-Altman analyses 31 were used to assess the variability in the ciliary body measurements. Statistics from a Bland-Altman analysis indicate how repeatable a measure is in absolute terms. The mean of the differences between the repeated measurements characterizes the bias in measurement due to drift in the measurements over time or investigator differences. A one-sample t-test was used to test whether the mean of the differences was zero. The mean of the differences and its standard deviation were used to construct 95% limits of agreement (LoA) (mean±[1.96×standard deviation]). The LoA characterize the expected differences between repeated measurements. They estimate the boundaries within which 95% of the differences should fall. The coefficient of repeatability (1.96×standard deviation of the differences) was also calculated. The difference between the two measurements versus the mean of the two measurements was graphed and visually inspected to determine if the repeatability of the measurement was related to the magnitude of the measurement. The following Bland-Altman comparisons were completed:

1. Evaluation of the repeatability of caliper and algorithm measurements
2. Comparison of caliper measurements taken from different investigators
3. Comparison of caliper and algorithm measurements
4. Comparison of simulated and investigator caliper measurements Additionally, the inventors sought to determine how within- and between-investigator differences in selecting the scleral spur would impact ciliary body thickness measurements made by the algorithm. The input to the algorithm is an image of the ciliary body. Factors that result in variability in the algorithm's measurements are the biological variability of the image's source (i.e., differences between subjects), the alignment during acquisition of each image, and the selection of the scleral spur within each image by an investigator. To assess the relative importance of the various sources of variability inventors fitted the following model:

$$CBT_{ijkl} = \mu + subject_i + image_{ij} + investigator_{ijk} + error_{ijkl}$$

$CBT_{ijkl}$ is the thickness measure derived from the jth image taken for subject i using the lth scleral spur selection by investigator k. $\mu$ is the population mean of the ciliary body thickness measurement, $subject_i$ is subject i's deviation from the population mean due to biological variability, $image_{ij}$ is the deviation from subject i's measure due to variation in acquisition of individual images of the ciliary body, $investigator_{ijk}$ is the deviation in the jth image from subject i due to bias in investigator k's selection of the scleral spur for the image, and $error_{ijkl}$ is random deviation from this bias for investigator k. $Subject_i$, $image_{ij}$ and $investigator_{ijk}$ were fitted as random effects and their variances estimated. For each CBT measurement inventors present the percent of total variation in the measurement that is attributable to each factor. The sum of the percent for investigator and error provide the percent of total variation due to scleral spur selection. All modeling was done in SAS using the MIXED procedure.

2) Impact of Number of Images on Repeatability

Interclass Correlation Coefficient (ICC) estimates were computed using parameters from the fitting of another random effects model. For a variable y (example, CBT2), the jth measurement for subject i was modeled as:

$$y_{ij} = \mu + \epsilon_{ij}$$

In the model $\mu$ is the population mean of the measurement and $\epsilon$ was the deviation from the mean of subject i's jth measure. The deviation from the mean ($\epsilon$) was decomposed into a deviation due to biological variability between subjects ($\delta_i$) and within-subject measurement error ($\xi_{ij}$). This decomposition led to the following multilevel representation of y:

$$y_{ij} = \mu + \delta i + \xi_{ij} \quad (1)$$

A metric of measurement repeatability is the ICC, which is the portion of overall score variance (given by the sum of the variances of $\delta$ and $\xi$) that is due to between-subject variance (given by the variance of $\delta$). To compute this proportion inventors fitted Equation 1 using the SAS procedure MIXED. The procedure provided estimates of total and between subject variance.

Inventors then computed estimates of what would happen if a measurement was a composite of multiple measurements of the variable on the same occasion. To obtain these estimates inventors made use of the results from the fitting of Equation 1. If z is the mean of n measures of y, the variance of z is the sum of the variance of $\delta$ and the variance of $\xi$ divided by n.

The use of a mean has no affect on biological variability, but decreases within-subject variability by a factor of n, making total variability the sum of the variance of $\delta$ and the variance of $\xi$ divided by n. Inventors used the estimates from the SAS MIXED procedure for the variance of $\delta$ and $\xi$, adjusting estimates of total variability for n=1 to 8 by using the sum of the variance of $\delta$ and the variance of $\xi$ divided by n, to generate the data for the curves presented in the results.

The intraclass correlation coefficient (ICC) was estimated for all thickness and area measurements. A higher ICC indicates a more consistent measurement. With higher ICC, the nuisance of measurement error within an individual is less likely to result in an error in the estimate of his relative ranking within the population. There is no consensus on what is an adequate ICC (range 0 to 1). Nunnally suggests that values greater than 0.80 are adequate for research tools.

B. Results

1) Semi-Automatic Algorithm Extraction

The semi-automatic algorithm was able to successfully outline the ciliary body allowing for further morphological study. The outlining procedure only failed on images where there were shadows due to eye lashes, on poor quality images due to eye movement, or when images were very tilted from poor subject alignment. The algorithm was successful in all images included in these tests, as all were aligned appropriately and free of shadows or eye movements. The thickness and cross-sectional area of the ciliary body were automatically measured at several points. Summary statistics for the ciliary body variables are presented in Table 1.

TABLE 1

Mean and SD of ciliary body thickness and cross-sectional area measurements for the caliper and algorithm measurement methods across all subjects

| Measurement | Experienced examiner caliper measurements | | Algorithm (refractive index, n = 1.00) | | Algorithm (refractive index, n = 1.38) | |
|---|---|---|---|---|---|---|
| | Mean | SD | Mean | SD | Mean | SD |
| CBT1 (mm) | 1.12 | 0.11 | 1.15 | 0.09 | 0.92 | 0.09 |
| CBT2 (mm) | 0.72 | 0.13 | 0.78 | 0.13 | 0.61 | 0.12 |
| CBT3 (mm) | 0.42 | 0.09 | 0.46 | 0.12 | 0.32 | 0.09 |
| CBTmax (mm) | NA | NA | 1.17 | 0.09 | 0.96 | 0.09 |
| CBA1 (mm$^2$) | NA | NA | 0.76 | 0.11 | 0.77 | 0.11 |
| CBA2 (mm$^2$) | NA | NA | 0.89 | 0.08 | 0.71 | 0.09 |
| CBA3 (mm$^2$) | NA | NA | 0.56 | 0.12 | 0.41 | 0.10 |

Algorithm measurements with a refractive index of n = 1 and n = 1.38 applied to the area of the sclera and ciliary body are both shown to allow for comparison with the caliper measurements (refractive index, n = 1).
NA, not available for this measurement method.

2) Caliper and Algorithm Measurement Variability

Results of the between-image repeatability analyses are presented in Table 2.

TABLE 2

Bland-Altman analyses of the repeatability of single ciliary body measurements made by an examiner and with the algorithm (difference = last of the six measurements − first of the six measurements)

| Measurement | Mean of the differences | SD of the differences | 95% Limits of agreement | | Coefficient of repeatability |
|---|---|---|---|---|---|
| | | | Lower bound | Upper bound | |
| Experienced examiner calipers | | | | | |
| CBT1 (mm) | −0.02 | 0.10 | −0.21 | 0.18 | 0.19 |
| CBT2 (mm) | −0.04 | 0.09 | −0.22 | 0.14 | 0.18 |
| CBT3 (mm) | −0.02 | 0.06 | 0.15 | 0.11 | 0.13 |

TABLE 2-continued

Bland-Altman analyses of the repeatability of single ciliary body measurements made by an examiner and with the algorithm (difference = last of the six measurements − first of the six measurements)

| Measurement | Mean of the differences | SD of the differences | 95% Limits of agreement Lower bound | 95% Limits of agreement Upper bound | Coefficient of repeatability |
|---|---|---|---|---|---|
| Semiautomatic algorithm | | | | | |
| CBT1 (mm) | 0.01 | 0.06 | −0.11 | 0.13 | 0.12 |
| CBT2 (mm) | −0.02 | 0.07 | −0.15 | 0.11 | 0.13 |
| CBT3 (mm) | −0.02 | 0.05 | −0.12 | 0.08 | 0.10 |
| CBTmax (mm) | 0.01 | 0.08 | −0.15 | 0.19 | 0.16 |
| CBA1 ($mm^2$) | 0.04 | 0.08 | −0.12 | 0.20 | 0.16 |
| CBA2 ($mm^2$) | −0.01 | 0.05 | −0.11 | 0.08 | 0.10 |
| CBA3 ($mm^2$) | −0.02 | 0.05 | −0.12 | 0.07 | 0.09 |

For both the calipers and the algorithm, the first and sixth images were compared. Visual inspection of the difference versus mean plots for the various algorithm thickness and area measurements did not reveal any relationship between the repeatability of a measurement and the magnitude of the measurement. The coefficient of repeatability, an indicator of measurement variability, was comparable across all variables, ranging from 0.09 mm to 0.19 mm. For some of the calipers and the algorithm measurements, the sixth image's measurements tended to be smaller than the first image's measurement, although the magnitude of the means of the differences was small compared to the magnitude of the measurement. None of the means of the differences were statistically different from zero after adjusting for multiple comparisons.

The between-investigator comparisons of the caliper measurements are shown in Table 3.

(t=3.2, p=0.004). The magnitude, however, of the means of the differences between investigators is small compared to the magnitude of the measurements (CBT1: −0.06 mm vs. 1.12 mm and CBT3: 0.03 mm vs. 0.42 mm, respectively).

To further assess the performance of the algorithm, inventors completed an analysis to determine the percent of total variance in ciliary body thickness measurements that is attributable to each of the potential sources of variability (Table 4). The variance attributable to differences across subjects, i.e., variance due to biological variability, was approximately 80% for all three thickness measurements. Overall, the percent of variation that was attributable to differences between two investigator's scleral spur selections was about the same size as that variability due to scleral spur selection on different occasions by the same investigator (range 1.5% or 3.8%), and

TABLE 3

Bland-Altman analyses of the agreement between the caliper measurements of the ciliary body made by the two different examiners (difference = inexperienced examiner − experienced examiner)

| Measurement (mm) | Mean of the differences | SD of the differences | 95% Limits of agreement Mean lower bound | 95% Limits of agreement Mean upper bound | Coefficient of repeatability |
|---|---|---|---|---|---|
| CBT1 | −0.06[a] | 0.08 | −0.22 | 0.10 | 0.16 |
| CBT2 | 0.01 | 0.08 | −0.14 | 0.16 | 0.15 |
| CBT3 | 0.03[b] | 0.06 | −0.08 | 0.13 | 0.11 |

[a] t = −5.7, p < 0.0001.
[b] t = 3.2, p = 0.004.

TABLE 4

Percent of total variance attributable to the each potential sources of variability in the execution of the algorithm

| | Potential sources of variability (%) | | | |
|---|---|---|---|---|
| Measurement location | Biological/inter-subject | Image acquisition | Between-examiners | Within-examiner |
| CBT1 | 82.3 | 12.5 | 1.5 | 3.8 |
| CBT2 | 79.4 | 15.6 | 1.2 | 3.7 |
| CBT3 | 79.6 | 14.9 | 2.7 | 2.9 |

Within-examiner variability can be interpreted as the variability associated with an examiner selecting the scleral spur location on two separate occasions and the between-examiner variability is the variability attributable to the differences in the scleral spur selection of two different examiners.

Visual inspection of Bland-Altman difference versus mean plots did not reveal any relationship between the magnitude of the measurement and the investigator agreement. The coefficient of repeatability was comparable across all variables. The experienced investigator made slightly thicker measurements at CBT1 (t=5.7, p<0.0001), and the inexperienced investigator made slightly thicker measurements at CBT3 this variability is very small when compared to the variability due to biological differences (~80%) or differences in image acquisition (~15%).

3) Impact of Number of Images on Repeatability

Figure 10:
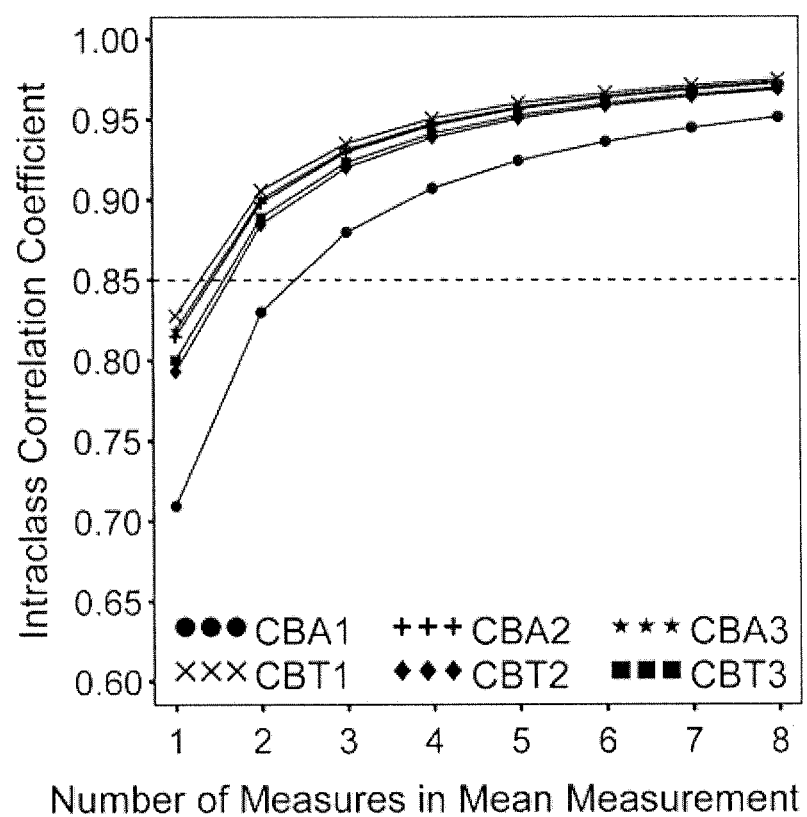
FIG. 10 illustrates the relationship between the number of images and interclass correlation between measurements.

The analysis in Table 4 shows that approximately 80% of the variability of the algorithm measurements is due to biological variability. The remaining 20%, due to positioning during image acquisition and within- and between-investigator differences, can be reduced by using the mean of multiple measurements. FIG. 10 illustrates the estimated increase in ICC if multiple images from the same subject are measured with the algorithm and the mean of those multiple measurements are used. If three images are used instead of one, all of the ciliary body measurements have an estimated ICC greater than 0.85.

4) Caliper and Algorithm Measurement Agreement

Table 5 is a summary of algorithm measurements compared to caliper measurements made by an experienced investigator.

TABLE 5

Bland-Altman analyses of the agreement between the semiautomatic algorithm and caliper measurements of the ciliary body (difference = algorithm measurements − experienced examiner caliper measurements)

| Measurement (mm) | Mean of the differences | SD of the differences | 95% Limits of agreement | | Coefficient of repeatability |
|---|---|---|---|---|---|
| | | | Lower bound | Upper bound | |
| CBT1 | 0.03 | 0.13 | −0.22 | 0.27 | 0.25 |
| CBT2 | 0.06[a] | 0.09 | −0.12 | 0.23 | 0.18 |
| CBT3 | 0.03[b] | 0.07 | NA | NA | 0.13 |

[a] $t = 5.9, p < 0.0001$.
[b] $t = 3.6, p < 0.001$.
NA, not applicable, the mean of the measurements was related to the difference between the measurements.

Figure 11:
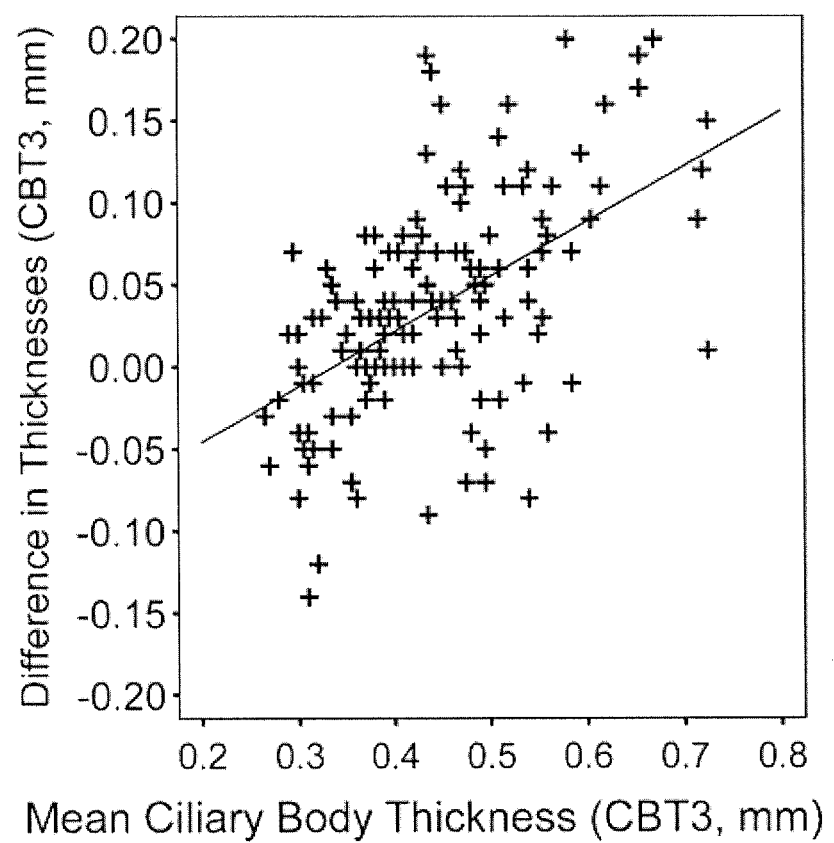
FIG. 11 illustrates the results of an experimental comparison between caliper measurements and measurements made using the present method.

For all thickness measurements, the algorithm provided on average a slightly larger estimate of thickness than the caliper measurement. (Note that a refractive index of n=1 was applied to the images used for both caliper and algorithm measurements because it is not possible to apply an appropriate refractive index to the ciliary body in the Visante™ software.) Visual inspection of Bland-Altman plots for CBT1 and CBT2 did not reveal any relationship between the difference in the measurements and the magnitude of the measurements. For CBT3, however, there was a trend. The algorithm provided thickness measurements that were increasingly thicker than the caliper measurements as the thickness of the ciliary body increased (FIG. 11).

It was expected that the algorithm measurements might be larger than the caliper measurements on average because the calipers cut across the ciliary muscle instead of following the scleral curvature (FIG. 1). A trend in the difference between the algorithm and caliper measurement was, however, unexpected and suggested that the problem depicted in FIG. 1b may become more pronounced in subjects with a thicker ciliary body. It was also possible, however, that there was a more fundamental problem. It might have been the case that the binary files used for the algorithm were different in image magnification or size than the image format used by the Visante™ software. To address this issue further, caliper measurements were simulated in Matlab® within the same outline that was used for the automatic algorithm, i.e., a straight line was used to find the position of CBT1, CBT2, and CBT3. In this analysis, the simulated caliper measurements were taken within the same image file type used for algorithm measurements.

A Bland-Altman agreement analysis was conducted to compare the simulated calipers to the experienced investigator's calipers from the Visante™ software (Table 6). While the mean of the differences at CBT3 was significantly different from zero, the magnitudes of all means of the differences were small. In addition, the coefficients of repeatability when comparing the simulated calipers to the experienced investigator's calipers (Table 6) were comparable to the coefficients of repeatability when comparing the experienced and inexperienced investigator's calipers (Table 3).

In addition to providing measurements of the ciliary body that generally agree well with Visante™ caliper measurements, the semi-automatic algorithm is acceptably repeatable. Within- and between-investigator variations in scleral spur selection represented a very small (6%) portion of the variance in the measurement when compared to the variance due to biological differences across subjects (80%). Any measurement of the ciliary body made with the semi-automatic algorithm should provide an ICC of 0.85 if investigators obtain three images of a subject's ciliary body and use the mean of the measurements. In an unpublished study, inventors were able to obtain six images of the ciliary body in first through fifth grade children during one testing session. Thus, inventors expect obtaining the three images required for this semi-automatic algorithm will be more than feasible in future studies of children.

A trend towards small differences was found in both the caliper and semi-automatic algorithm measurements when the first and last images from the measurements session were compared. Although the differences were not statistically significant after adjusting for multiple comparisons, the trend may indicate that the vertical alignment of the subjects may have slipped slightly during testing, resulting in a scanning position above or below the midpoint of the pupil by the time the last image was captured. Thus, when this vertical slippage occurred, it resulted in a significantly smaller thickness or cross-sectional area measurement in some cases.

While a corneal reflex, i.e., a bright white line in the middle of the image, provides a landmark for Visante™ measurements of the crystalline lens thickness, there is no such landmark to reference ciliary body imaging. The investigator may adapt to this by checking subject alignment between images. Because only three images are needed in future studies that use the semi-automatic algorithm, rather than the six images obtained for this study, alignment may be easier to maintain. In addition, inventors are aware that the latest version of Visante™ software, Version 3.0, captures an image of the eye with a visible record of the scanning beam placement. This will facilitate post-examination evaluation of image capture. Images where the alignment of the eye is not at the mid-point of the pupil could be excluded from analysis, and this might reduce the variability in the measurement that is associated with image acquisition differences.

V. Computerized Implementations

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various embodiments with various modifications as are suited to the particular use contemplated.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 12:
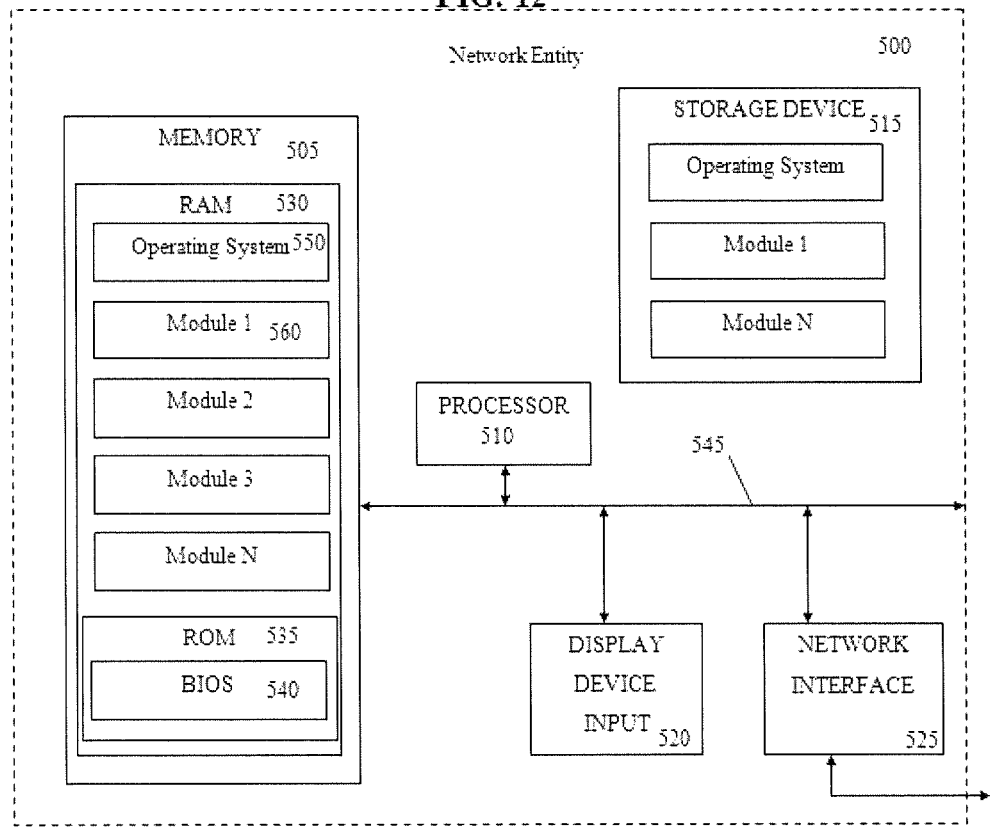
FIG. 12 is a schematic of a computer system for implementing a method of the present invention.

Referring now to FIG. 12, a schematic diagram of a central server 500, or similar network entity, configured to implement a soft tissue image measurement system, according to one implementation of the invention, is provided. As used herein, the designation "central" merely serves to describe the common functionality the server provides for multiple clients or other computing devices and does not require or infer any centralized positioning of the server relative to other computing devices. As may be understood from FIG. 12, in this implementation, the central server 500 may include a processor 510 that communicates with other elements within the central server 500 via a system interface or bus 545. Also included in the central server 500 may be a display device/input device 520 for receiving and displaying data. This display device/input device 520 may be, for example, a keyboard or pointing device that is used in combination with a monitor. The central server 500 may further include memory 505, which may include both read only memory (ROM) 535 and random access memory (RAM) 530. The server's ROM 535 may be used to store a basic input/output system 540 (BIOS), containing the basic routines that help to transfer information across the one or more networks.

In addition, the central server 500 may include at least one storage device 515, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the art, each of these storage devices 515 may be connected to the system bus 545 by an appropriate interface. The storage devices 515 and their associated computer-readable media may provide nonvolatile storage for a central server. It is important to note that the computer-readable media described above could be replaced by any other type of computer-readable media known in the art. Such media include, for example, magnetic cassettes, flash memory cards and digital video disks. A number of program modules may be stored by the various storage devices and within RAM 530. Such program modules may include an operating system 550 and a plurality of one or more (N) modules 560. The modules 560 may control certain aspects of the operation of the central server 500, with the assistance of the processor 510 and the operating system 550. For example, the modules may perform the functions described above and illustrated by the figures and other materials disclosed herein.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The implementation was chosen and described in order to best explain the principles of the invention and the practical application, and to enable others of ordinary skill in the art to understand the invention for various embodiments with various modifications as are suited to the particular use contemplated.

Portions of this application were excerpted from an article entitled "Semiautomatic Extraction Algorithm for Images of the Ciliary Muscle," by Chiu-Yen Kao et al. in Optometry and Vision Science, 2011; 88:275-289.

The invention claimed is:

1. A method of measuring a tissue structure, the method comprising:
   obtaining image data of the tissue structure;
   identifying an anatomical landmark in the image data of the tissue structure;
   applying a first geometric shape with at least one linear portion to the image data of the tissue structure based on the anatomical landmark;
   applying a second geometric shape with at least one curved portion to the image data of the tissue structure based on the anatomical landmark; and
   segmenting a first substructure of the image data from a second substructure of the image data using the first and second geometric shapes.

2. A method of claim 1, further comprising obtaining background image data with the image data of the tissue structure and separating the background image data from the image data of the tissue structure.

3. A method of claim 1, wherein the tissue structure is within the eye.

4. A method of claim 3, wherein the first substructure is a sclera and the second substructure is a ciliary body.

5. A method of claim 4, wherein the anatomical landmark is a scleral spur.

6. A method of claim 1, further comprising downsizing the image data.

7. A method of claim 1, wherein each geometric shape defines a segmentation region.

8. A method of claim 1, wherein the second geometric shape is an approximation of an ocular structure.

9. A method of claim 1, wherein the first geometric shape is a diamond shape.

10. A method of claim 9, wherein applying the first geometric shape includes positioning the diamond shape on an apex of the tissue structure.

11. A method of claim 10, wherein the tissue structure is a ciliary body.

12. A method of claim 11, further comprising dilating a threshold region.

13. A method of claim 12, wherein dilating the threshold region includes dilating with a rolling ball.

14. A method of claim 13, wherein applying the first geometric shape and dilating the threshold region include forming an outline of at least a portion of the ciliary body.

15. A method of claim 14, wherein applying the second geometric shape includes fitting a curve through the anatomical landmark.

16. A method of claim 15, wherein the anatomical landmark is a scleral spur.

17. A method of claim 16, further comprising locating a second and third points using the outline.

18. A method of claim 17, wherein fitting the curve includes fitting a parabola through the scleral spur and third point.

19. A method of claim 18, further comprising identifying a fourth point positioned above a straight line extending through the scleral spur and the third point.

20. A method of claim 19, wherein fitting the parabola includes fitting through the fourth point.

21. A method of claim 20, wherein the parabola defines an upper boundary between the ciliary boundary and the sclera.

22. A method of claim 21, further comprising adjusting the parabola by minimizing the energy of the image data.

23. A method of claim 22, further comprising applying different indexes of refraction to the sclera and the ciliary body.

24. A method of claim 21, further comprising adjusting the parabola using a least squares fit.

25. A method of claim 24, further comprising removing the iris using the second point and the scleral spur.

26. A method of claim 25, further comprising measuring at least one thickness of the ciliary body.

27. A method of claim 26, further comprising measuring an area of the ciliary body.

28. A method of measuring an ocular tissue structure, the method comprising:
   obtaining image data of the tissue structure;
   identifying an anatomical landmark in the image data of the tissue structure;
   applying a first geometric shape to the image data of the tissue structure based on the anatomical landmark;
   applying a second geometric shape to the image data of the tissue structure based on the anatomical landmark; and
   segmenting a sclera of the image data from a ciliary body of the image data using the first and second geometric shapes.

29. A method of claim 28, wherein the ciliary body is a ciliary muscle.

* * * * *

UNITED STATES PATENT AND TRADEMARK OFFICE
CERTIFICATE OF CORRECTION

PATENT NO. : 9,060,717 B2
APPLICATION NO. : 13/757243
DATED : June 23, 2015
INVENTOR(S) : Melissa D. Bailey et al.

Page 1 of 1

It is certified that error appears in the above-identified patent and that said Letters Patent is hereby corrected as shown below:

In the Specification

Column 1, Lines 14-17, replace the ACKNOWLEDGEMENT OF GOVERNMENT SUPPORT paragraph with the following paragraph:
--This invention was made with government support under EY019097, EY014792, EY013359, EY071510, and RR025754 awarded by the National Institutes of Health. The government has certain rights in the invention.--

Signed and Sealed this
Twenty-ninth Day of June, 2021

Drew Hirshfeld
*Performing the Functions and Duties of the*
*Under Secretary of Commerce for Intellectual Property and*
*Director of the United States Patent and Trademark Office*